United States Patent
Abe et al.

(10) Patent No.: US 8,633,698 B2
(45) Date of Patent: Jan. 21, 2014

(54) GRADIENT COIL DEVICE, MAGNETIC RESONANCE IMAGING DEVICE, AND METHOD OF DESIGNING COIL PATTERN

(75) Inventors: Mitsushi Abe, Hitachinaka (JP); Yukinobu Imamura, Hitachi (JP); Akira Kurome, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 960 days.

(21) Appl. No.: 12/644,470

(22) Filed: Dec. 22, 2009

(65) Prior Publication Data
US 2010/0194393 A1    Aug. 5, 2010

(30) Foreign Application Priority Data
Dec. 22, 2008   (JP) ................. 2008-326130

(51) Int. Cl.
*G01V 3/00*      (2006.01)

(52) U.S. Cl.
USPC .......................................... 324/318; 324/322

(58) Field of Classification Search
USPC ......................................... 324/318, 322, 321
See application file for complete search history.

(56) References Cited

U.S. PATENT DOCUMENTS

| | | | | |
|---|---|---|---|---|
| 5,124,652 A | * | 6/1992 | Aubert | 324/318 |
| 5,581,187 A | * | 12/1996 | Pausch | 324/318 |
| 6,144,204 A | * | 11/2000 | Sementchenko | 324/318 |
| 6,529,003 B2 | | 3/2003 | Goto et al. | |
| 7,932,722 B2 | * | 4/2011 | Amm et al. | 324/318 |
| 7,936,233 B2 | * | 5/2011 | Vellas et al. | 333/17.3 |

FOREIGN PATENT DOCUMENTS

| | | |
|---|---|---|
| JP | 5-308017 | 11/1993 |
| JP | 06-014900 | 1/1994 |
| JP | 07-194574 | 8/1995 |
| JP | 2001-413 | 1/2001 |
| JP | 2001-353137 | 12/2001 |

OTHER PUBLICATIONS

JP Office Action for Japanese Application No. 2011-183358, issued on Dec. 11, 2012.
C.H. Oh, "Complete Design Equation For Gradient Coil Design Using Loop-Current Elements", Proceedings of the International Society for Magnetic Resonance in Medicine, Apr. 3, 2000, p. #330.

* cited by examiner

*Primary Examiner* — Louis Arana
(74) *Attorney, Agent, or Firm* — Antonelli, Terry, Stout & Kraus, LLP.

(57) ABSTRACT

There is provided a gradient coil device which can suppress any generation of an error magnetic field and thus an eddy current, and which can improve the image quality of a cross-sectional image. An MRI device includes a first coil generating a linear magnetic field distribution at an imaging region of the MRI device, and a second coil which suppresses any leakage of a magnetic field from the first coil to a static-magnetic-field coil device that generates a uniform magnetic field distribution at the imaging region.

10 Claims, 13 Drawing Sheets

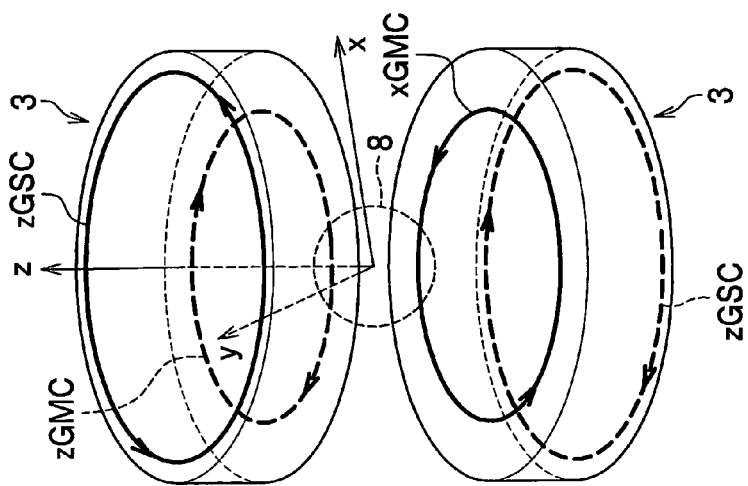
FIG.4A  FIG.4B  FIG.4C
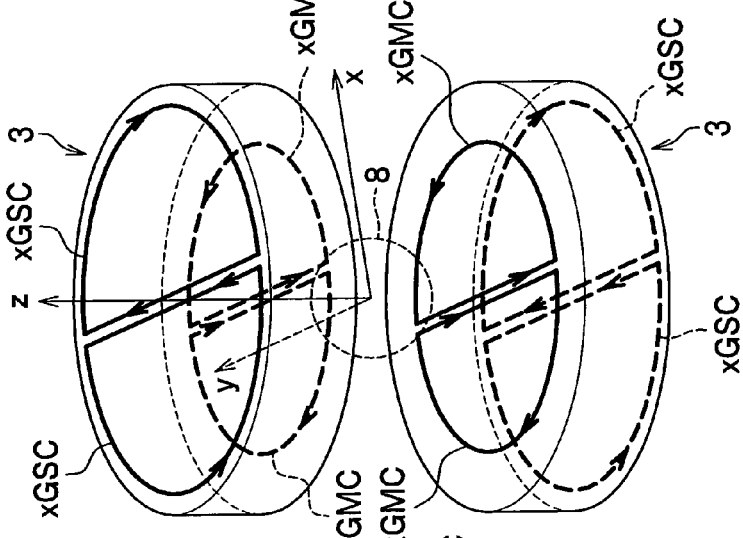
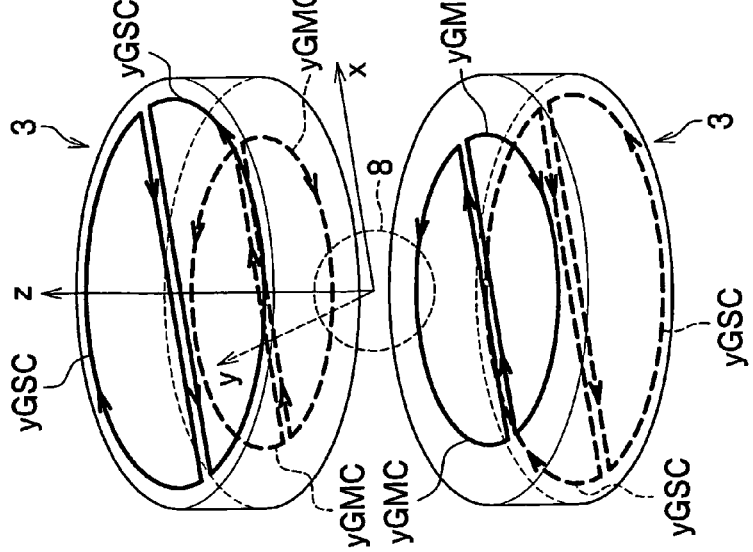

POSITION ON VACUUMED CONTAINER
(CONDUCTIVE OBJECT)

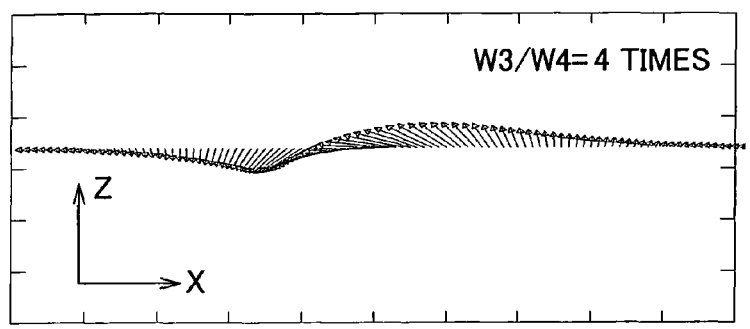
FIG.14A  W3/W4= 4 TIMES
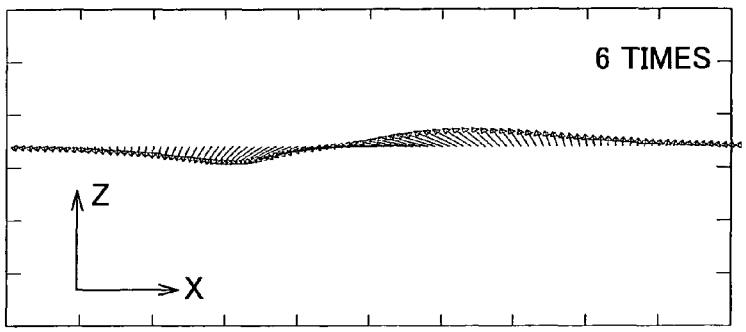
FIG.14B  6 TIMES
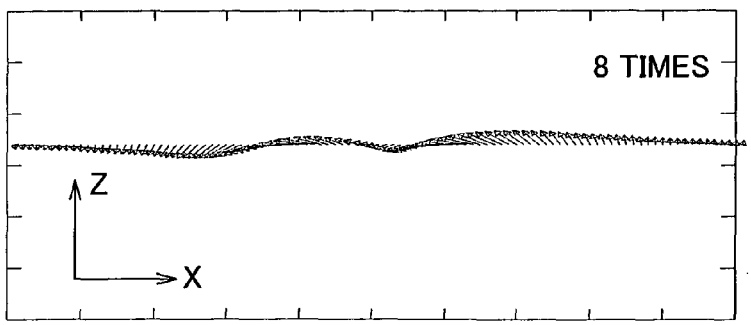
FIG.14C  8 TIMES
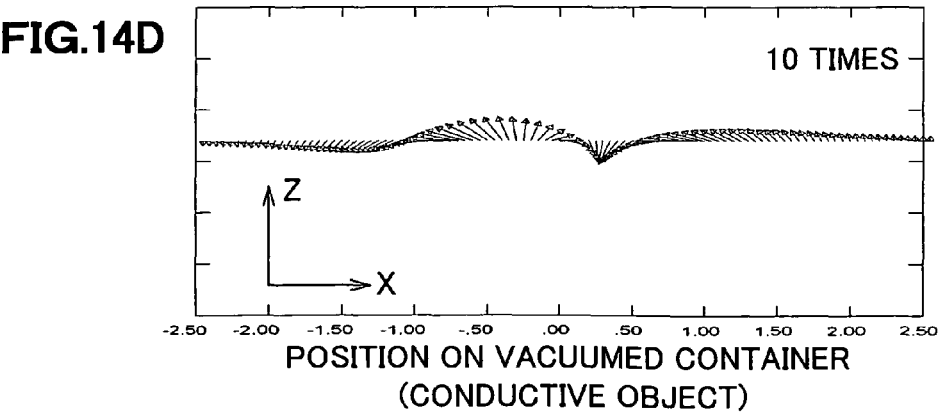
FIG.14D  10 TIMES
POSITION ON VACUUMED CONTAINER
(CONDUCTIVE OBJECT)

GRADIENT COIL DEVICE, MAGNETIC RESONANCE IMAGING DEVICE, AND METHOD OF DESIGNING COIL PATTERN

BACKGROUND OF THE INVENTION

1. Field of the Invention

The present invention relates to a magnetic resonance imaging (hereinafter, "MRI") device, a gradient coil device used in the MRI device, and a method of designing a coil pattern of a coil used in the gradient coil device.

2. Description of the Related Art

MRI devices obtains a cross-sectional image of an object under test indicating physical and chemical characteristics thereof by utilizing nuclear magnetic resonance phenomena which occurs when the object under test arranged in a uniform static magnetic field is irradiated with high-frequency pulses, and such devices are used for, in particular, medical purposes. MRI devices generally include static-magnetic-field coil devices which generate a uniform static magnetic field in an imaging region where the object under test is put in, gradient coil devices which generate a pulsed gradient magnetic field having magnetic field intensity spatially inclined in order to add positional information to the imaging region, RF coils emitting high-frequency pulses to the object under test, a reception coil which receives a magnetic resonance signal from the object under test, and a computer system which processes the received magnetic resonance signal to display the cross-sectional image.

JP2001-353137A discloses a gradient coil device which generates a gradient magnetic field having magnetic field intensity linearly inclined in order to improve the performances of the MRI devices (see FIG. 1).

SUMMARY OF THE INVENTION

Conventional gradient coil has a coil with a complex coil pattern. In such a coil pattern, a plurality of looped main lines each having an opened part are multiply arranged on one plane in such a way that one main line is arranged inwardly of another adjacent main line, and a connecting line for connecting adjacent main lines and a return line running from an inward main line to an outward main line are provided so as to partially overlap with each other.

As the plurality of main lines each formed in a loop shape with an opened part are multiply arranged and adjacent main lines are connected together by the connecting line, a spiral coil pattern having multiple main lines connected together is formed. Providing the return line allows a current to flow through the plurality of main lines. According to the conventional gradient coils, however, it is designed to generate a linear gradient magnetic field when a current flows through only the plurality of main lines. Therefore, when a current flows through the connecting line and the return line, this causes generation of an error magnetic field. Such an error magnetic field generates an eddy current at the static-magnetic-field coil devices, and such an eddy current may generate a magnetic field which disturbs the cross-sectional image in the imaging region.

Therefore, it is an object of the present invention to provide a gradient coil device, an MRI device, and a coil pattern designing method which can suppress any generation of an error magnetic field and thus an eddy current, and which can improve the image quality of a cross-sectional image.

In order to achieve the above object, the present invention provides a gradient coil device including: a first coil which generates a linear magnetic field distribution at an imaging region of a magnetic resonance imaging device; and a second coil which suppresses any leakage of a magnetic field from the first coil to a static-magnetic-field coil that generates a uniform magnetic field distribution at the imaging region, in which a connecting line part of at least either one of the first coil and the second coil which intersects with a return line from a spiral coil pattern meanders.

Also, the present invention provides a gradient coil device including: a first coil which generates a linear magnetic field distribution at an imaging region of a magnetic resonance imaging device; and a second coil which suppresses any leakage of a magnetic field from the first coil to a static-magnetic-field coil that generates a uniform magnetic field distribution at the imaging region, in which a width of a connecting line part of at least either one of the first coil and the second coil which intersects with a return line from a spiral coil pattern is greater than or equal to four times and less than or equal to ten times than a width of the return line.

Also, the present invention provides a gradient coil device including: a first coil which generates a linear magnetic field distribution at an imaging region of a magnetic resonance imaging device; and a second coil which suppresses any leakage of a magnetic field from the first coil to a static-magnetic-field coil that generates a uniform magnetic field distribution at the imaging region, in which at least either one of the first coil and the second coil includes a coil pattern having an bypassed interval which intersects with a feeder line to a spiral coil pattern and a return line from the coil pattern.

Also, the present invention provides a coil pattern designing method for at least either one of a first coil which generates a linear magnetic field distribution at an imaging region of a magnetic resonance imaging device and a second coil which suppresses any leakage of a magnetic field to a static-magnetic-field coil device that generates a uniform magnetic field distribution at the imaging region, the method including the steps of: calculating an error magnetic field at the static-magnetic-field coil device based on an initial coil pattern prepared beforehand; calculating a correction current component to cancel the error magnetic field; and deforming the initial coil pattern based on the correction current component. Further, the present invention provides a gradient coil device or a magnetic resonance imaging device including at least either one of a first coil and a second coil, which are designed and manufactured by the coil pattern designing method According to the present invention, there are provided a gradient coil device, an MRI device, and a coil pattern designing method which can suppress any generation of an error magnetic field and thus an eddy current, and which can improve the image quality of a cross-sectional image.

BRIEF DESCRIPTION OF THE DRAWINGS

FIG. 4A is a diagram showing arrangements of y-direction gradient-magnetic-field main coils and y-direction gradient-magnetic-field shield coils in the gradient coil devices of the first embodiment;

FIG. 4B is a diagram showing arrangements of x-direction gradient-magnetic-field main coils and x-direction gradient-magnetic-field shield coils in the gradient coil devices of the first embodiment;

FIG. 4C is a diagram showing arrangements of z-direction gradient-magnetic-field main coils and z-direction gradient-magnetic-field shield coils in the gradient coil devices of the first embodiment;

FIGS. 14A to 14D are distribution charts of error magnetic field components generated by a return line and a first connecting line over a vacuumed container (conductive object), where FIG. 14A is for a case in which a ratio of a first connecting width W3 relative to a width W4 of the return line is four times, FIG. 14B is for a case in which the ratio of the first connecting width W3 relative to the width W4 of the return line is six times, FIG. 14C is for a case in which the ratio of the first connecting width W3 relative to the width W4 of the return line is eight times, and FIG. 14D is for a case in which the ratio of the first width W3 relative to the width W4 of the return line is ten times.

DETAILED DESCRIPTION OF THE PREFERRED EMBODIMENTS

Figure 1:
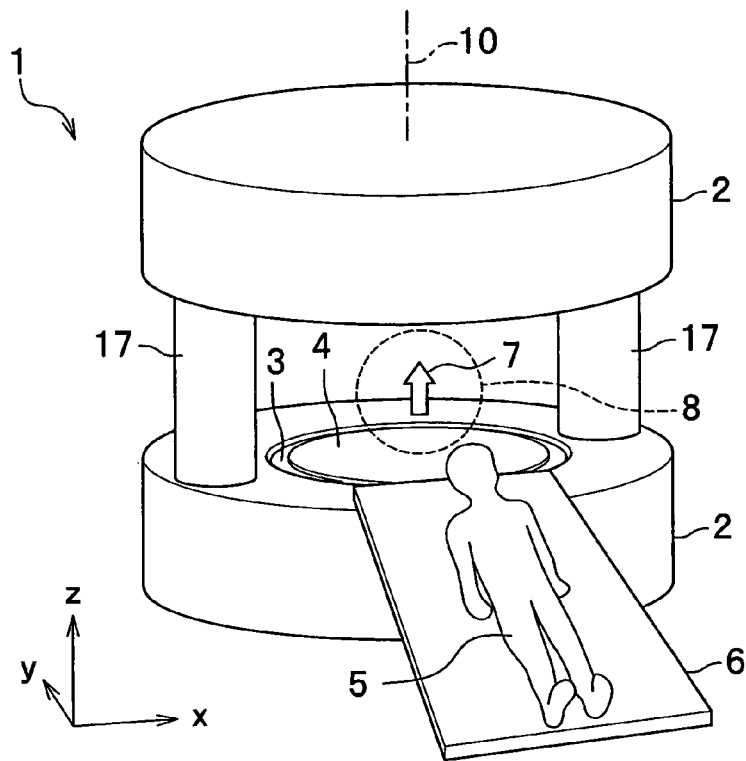
FIG. 1 is a perspective view showing an MRI (magnetic resonance imaging) device according to a first embodiment of the present invention.

An explanation will be given of embodiments of the present invention with reference to the accompanying drawings. Note that the same structural elements will be denoted by the same reference numerals in the drawings, and a duplicated explanation will be omitted.

First Embodiment

FIG. 1 is a perspective view showing an MRI (magnetic resonance imaging) device 1 according to the first embodiment of the present invention. The MRI device 1 is a vertical magnetic field type that a static magnetic field 7 is directed in the vertical direction. The MRI device 1 includes a pair of upper and lower static-magnetic-field coil devices 2 which are arranged above and below an imaging region 8 where an object 5 under test (hereinafter, object 5) lying down a bed 6 is put in, and which generate the uniform static magnetic field 7 in the imaging region 8, connection poles 17 which supports the pair of upper and lower static-magnetic-field coil devices 2 so as to be apart from each other, gradient coil devices 3 which generate a pulsed gradient magnetic field having a magnetic field intensity spatially inclined in order to add positional information to the imaging region 8, RF coils 4 which emit a high-frequency pulse to the object 5 put in the imaging region 8, a reception coil (not shown) which receives a magnetic resonance signal from the object 5, and a computer system (not shown) which processes the received magnetic resonance signal so as to display a cross-sectional image of the object 5. The pair of upper and lower static-magnetic-field coil devices 2, the gradient coil devices 3, and the RF coils 4 are formed in a disk (circular cylindrical) shape with a symmetrical axis 10 being as a common axis. The object 5 is delivered to the imaging region 8 by the movable bed 6, and the pair of upper and lower static-magnetic-field coil devices 2 are connected together by merely slim connection poles 17, so that the object 5 can look around, resulting in reduction of the fear of closed space. Moreover, in order to facilitate understanding for the following explanation, a z-axis is set in the vertical direction which is parallel and conforms to the symmetrical axis 10, and a x-axis and a y-axis are set in the horizontal direction so as to intersect with each other at right angle.

Figure 2:
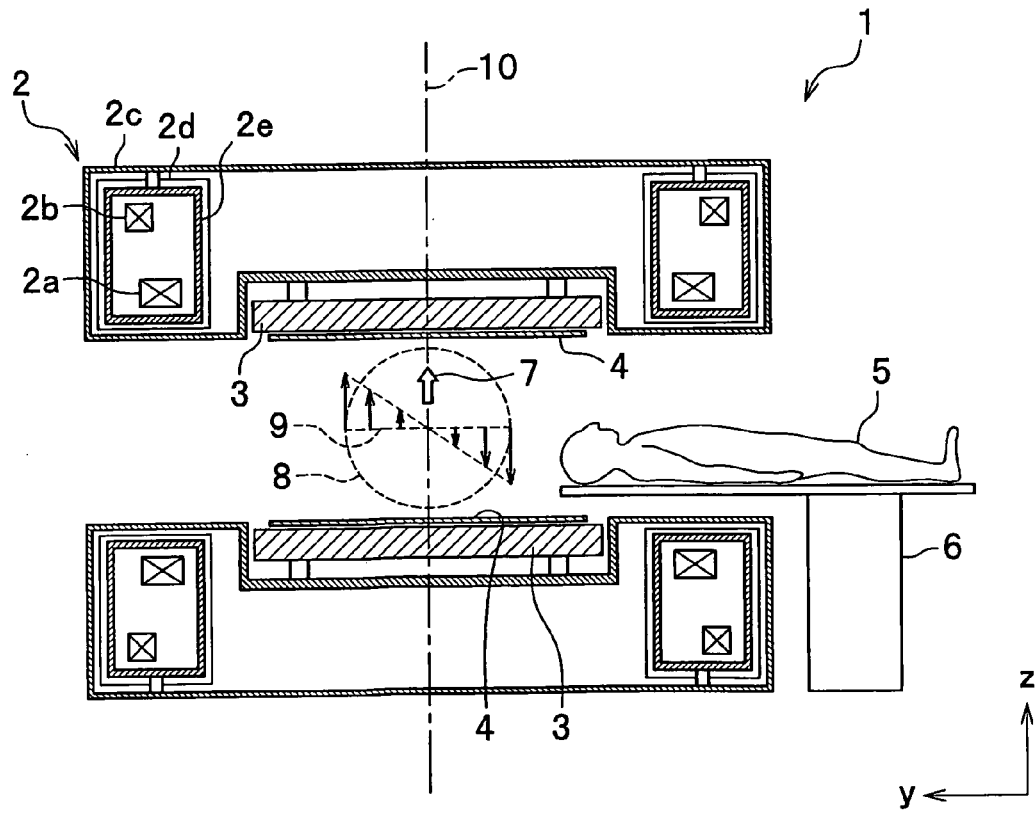
FIG. 2 is a cross-sectional view of the MRI device of the first embodiment along a y-z plane including a symmetrical axis (z-axis)

FIG. 2 is a cross-sectional view of the MRI device 1 of the first embodiment along a y-z plane including the symmetrical axis 10 (z-axis). The pair of upper and lower static-magnetic-field coils 2 include a pair of upper and lower static-magnetic-field main coils 2a, and a pair of upper and lower static-magnetic-field shield coils 2b. The pair of upper and lower static-magnetic-field main coils 2a and the pair of upper and lower static-magnetic-field shield coils 2b are formed in an annular shape with the symmetrical axis 10 being as a common central axis. The pair of upper and lower static-magnetic-field main coils 2a and the pair of upper and lower static-magnetic-field shield coils 2b are housed in a container with a three-layer structure. The pair of upper and lower static-magnetic-field main coils 2a and the pair of upper and lower static-magnetic-field shield coils 2b are housed in a pair of upper and lower refrigerant containers 2e together with a liquid helium (He) which serves as the refrigerant. Each refrigerant container 2e is wrapped by a heat radiation shield 2d which blocks heat radiation toward the interior of the refrigerant container 2e. A vacuumed container 2c houses the refrigerant container 2e and the heat radiation shield 2d thereinside which is in a vacuumed condition. Because the vacuumed container 2c is in the vacuumed condition, even if the vacuumed container 2c is arranged in a room at a normal room temperature, very little heat in the room is transferred to the refrigerant container 2e by heat conduction or heat convection. Moreover, the heat radiation shield 2d also suppresses any transfer of heat from the vacuumed container 2c to the refrigerant container 2e by heat radiation. Accordingly, the pair of static-magnetic-field main coils 2a and the pair of static-magnetic-field shield coils 2b can be stably set to an extremely low temperature due to the temperature of the refrigerant, and can function as superconductive electric magnets. The refrigerant container 2e, the heat radiation shield 2d, and the vacuumed container 2c are formed of a nonmagnetic material so that no force originating from a magnetic field applies thereto, and are formed of a nonmagnetic metal from the standpoint of easiness of work. Accordingly, a current, in particular, an eddy current may flow through the refrigerant container 2e, the heat radiation shield 2d, and the vacuumed container 2c.

The gradient coil devices 3 also include a pair of upper and lower coil pieces, and the pair of upper and lower gradient coil devices 3 are arranged above and below the imaging region 8. The RF coils 4 also include a pair of upper and lower coil pieces, and the pair of upper and lower RF coils 4 are arranged above and below the imaging region 8. The upper coil piece of the pair of upper and lower gradient coil devices 3 is arranged between the upper static-magnetic-field coil device 2 and the upper RF coil 4 in such a manner as to be arranged in the vicinity of both coils. Likewise, the lower coil piece of the pair of upper and lower gradient coil devices 3 is arranged between the lower static-magnetic-field coil device 2 and the lower RF coil 4 in such a manner as to be arranged in the vicinity of both coils. The pair of upper and lower gradient coil devices 3 generate a pulsed gradient magnetic field 9 having a magnetic field intensity, directed in the same direction as the static magnetic field 7, and inclined in an arbitrary direction. The gradient coil devices 3 has a function of generating the gradient magnetic field 9 independent in three directions of a x-direction, a y-direction, and a z-direction in such a manner as to overlap the static magnetic field 7. FIG. 2 shows the gradient magnetic field 9 inclined in the y-direction.

Figure 3:
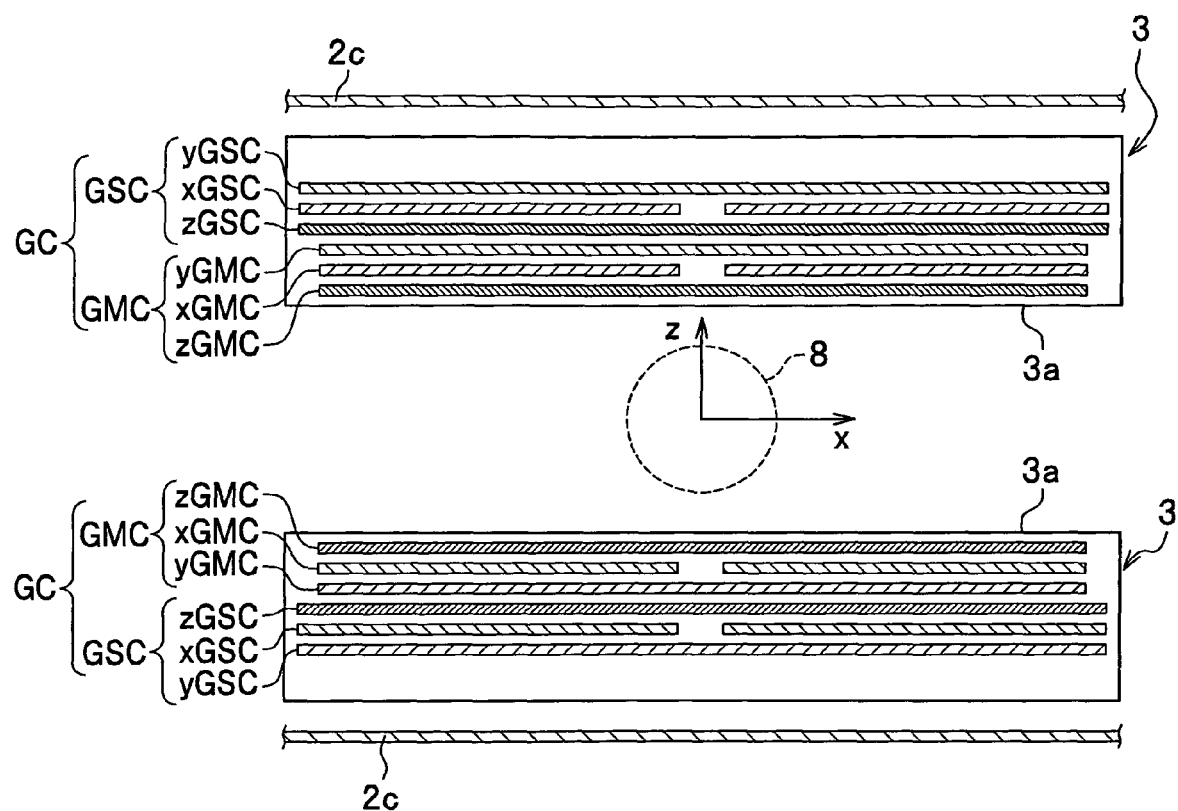
FIG. 3 is a cross-sectional view showing a gradient coil of the first embodiment.

FIG. 3 is a cross-sectional view showing the pair of upper and lower gradient coil devices 3. The gradient coil devices 3 include a pair of upper and lower gradient coils GC arranged above and below the imaging region 8. The pair of upper and lower gradient coils GC include a pair of upper and lower gradient-magnetic-field main coils (first coils) GMC arranged above and below the imaging region 8, and a pair of upper and lower gradient-magnetic-field shield coils (second coils) GSC arranged above and below the imaging region 8. The pair of upper and lower gradient-magnetic-field main coils GMC above and below the imaging region 8 are arranged between the pair of upper and lower gradient-magnetic-field shield coils (second coils) GSC. The upper gradient-magnetic-field main coil GMC and the upper gradient-magnetic-field shield coil GSC are supported with each other via a support member 3a. Likewise, the lower gradient-magnetic-field main coil GMC and the lower gradient-magnetic-field shield coil GSC are supported with each other via the support member 3a. The upper gradient coil device 3 (in particular, the upper gradient-magnetic-field shield coil GSC) is arranged in the vicinity of the upper static-magnetic-field coil device 2 (in particular, the upper vacuumed container 2c). Likewise, the lower gradient coil device 3 (in particular, the lower gradient-magnetic-field shield coil GSC) is arranged in the vicinity of the lower static-magnetic-field coil 2 (in particular, the lower vacuumed container 2c).

The pair of upper and lower gradient-magnetic-field main coils GMC includes a pair of upper and lower x-direction gradient-magnetic-field main coils xGMC which generate a gradient magnetic field linearly changing in the x-direction and which are arranged above and below the imaging region 8, a pair of upper and lower y-direction gradient-magnetic-field main coils yGMC which generate a gradient magnetic field linearly changing in the y-direction and which are arranged above and below the imaging region 8, and a pair of upper and lower z-direction gradient-magnetic-field main coils zGMC which generate a gradient magnetic field linearly changing in the z-direction and which are arranged above and below the imaging region 8. Each of the x-direction gradient-magnetic-field main coil xGMC, the y-direction gradient-magnetic-field main coil yGMC, and the z-direction gradient-magnetic-field main coil zGMC forms a layer (total: three layers) for each of the pair of the gradient coil devices 3, the three layers of the gradient-magnetic-field main coils xGMC, yGMC, and zGMC are formed as a pair, and such three layers are stacked together for each pair with an insulation layer of the support member 3a intervening in the z-direction.

The pair of upper and lower gradient-magnetic-field shield coils GSC include a pair of upper and lower x-direction gradient-magnetic-field shield coils x which suppress any leakage of the magnetic field generated by the x-direction gradient-magnetic-field main coils xGMC to the surroundings and which are arranged above and below the imaging region 8, a pair of upper and lower y-direction gradient-magnetic-field shield coils yGSC which suppress any leakage of the magnetic field generated by the y-direction gradient-magnetic-field main coils yGMC to the surroundings and which are arranged above and below the imaging region 8, and a pair of upper and lower z-direction gradient-magnetic-field shield coils zGSC which suppress any leakage of the magnetic field generated by the z-direction gradient-magnetic-field main coils zGMC and which are arranged above and below the imaging region 8. Each of the x-direction gradient-magnetic-field shield coil xGSC, the y-direction gradient-magnetic-field shield coil yGSC, and the x-direction gradient-magnetic-field shield coil zGSC forms a layer (total: three layers) for each of the pair of gradient coil devices 3, the three layers of the gradient-magnetic-field shield coils xGSC, yGSC, and zGSC are formed as a pair, and such three layers are stacked together for each pair with the insulating layer of the support member 3a intervening in the z-direction.

FIG. 4A is a diagram showing arrangements of the y-direction gradient-magnetic-field main coils yGMC and y-direction gradient-magnetic-field shield coils yGSC. The y-direction gradient-magnetic-field main coils yGMC are arranged, two by two (total: four), on each of two disk layers (not shown) having the z-axis as the central axis. Each of the four y-direction gradient-magnetic-field main coils yGMC is a spiral and sectorial coil in a substantially semicircular shape. The shape of such a spiral is not illustrated, and only a direction of a flow of a current is roughly illustrated. The four y-direction gradient-magnetic-field main coils yGMC can be divided two by two on a x-y plane, and have a plane-symmetrical structure relative to such a plane. Moreover, the four y-direction gradient-magnetic-field main coils yGMC can be divided two by two on a z-x plane, and have a plane-symmetrical structure relative to such a plane. Note that an arrow in the figure indicates the direction of a current flowing through the coil, and so forth in the following figures.

The y-direction gradient-magnetic-field shield coils yGSC are arranged, two by two (total: four), for each of two disk layers (not shown) having the z-axis as the central axis. Each of the four y-direction gradient-magnetic-field shield coils yGSC is a spiral and sectorial coil in a substantially semicircular shape, and so arranged as to cover the corresponding y-direction gradient-magnetic-field main coil yGMC. The shape of such a spiral is not illustrated, and only the direction of a flow of a current is roughly illustrated. The four y-direction gradient-magnetic-field shield coils yGSC can be divided two by two on a x-y plane, and have a plane-symmetrical structure relative to such a plane. Moreover, the four y-direction gradient-magnetic-field shield coils yGSC can be divided two by two on a z-x plane, and have a plane-symmetrical structure relative to such a plane.

FIG. 4B is a diagram showing arrangements of the x-direction gradient-magnetic-field main coils xGMC and x-direction gradient-magnetic-field shield coils xGSC. The x-direction gradient-magnetic-field main coils xGMC are arranged, two by two (total: four), for each of two disk layers (not shown) having the z-axis as the central axis. Each of the four x-direction gradient-magnetic-field main coils xGMC is a spiral and sectorial coil in a substantially semicircular shape. The shape of such a spiral is not illustrated, and only a direction of a flow of a current is roughly illustrated. The four x-direction gradient-magnetic-field main coils xGMC can be divided two by two on a x-y plane, and have a plane-symmetrical structure relative to such a plane. Moreover, the four x-direction gradient-magnetic-field main coils xGMC can be divided two by two on a y-z plane, and have a plane-symmetrical structure relative to such a plane.

The x-direction gradient-magnetic-field shield coils xGSC are arranged, two by two (total: four), for each of two disk layers (not shown) having the z-axis as the central axis. Each of the four x-direction gradient-magnetic-field shield coils xGSC is a spiral and sectorial coil in a substantially semicircular shape, and so arranged as to cover the corresponding x-direction gradient-magnetic-field main coil xGMC. The shape of such a spiral is not illustrated, and only the direction of a flow of a current is roughly illustrated. The four x-direction gradient-magnetic-field shield coils xGSC can be divided two by two on a x-y plane, and have a plane-symmetrical structure relative to such a plane. Moreover, the four x-direction gradient-magnetic-field shield coils xGSC can be divided two by two on a y-z plane, and have a plane-symmetrical structure relative to such a plane.

FIG. 4C is a diagram showing arrangements of the z-direction gradient-magnetic-field main coils zGMC and z-direction gradient-magnetic-field shield coils zGSC. The z-direction gradient-magnetic-field main coils zGMC are arranged, one by one (total: two), for each of two disk layers (not shown) having the z-axis as the central axis. Each of the two z-direction gradient-magnetic-field main coils zGMC is a spiral and circular coil. The shape of such a spiral is not illustrated, and only a direction of a flow of a current is roughly illustrated. The two z-direction gradient-magnetic-field main coils zGMC can be divided one by one on a x-y plane, and have a plane-symmetrical structure relative to such a plane.

The z-direction gradient-magnetic-field shield coils zGSC are arranged, one by one (total: two), for each of two disk layers (not shown) having the z-axis as the central axis. Each of the two z-direction gradient-magnetic-field shield coils zGSC is a spiral and circular coil, and so arranged as to cover the corresponding z-direction gradient-magnetic-field main coil zGMC. The shape of such a spiral is not illustrated, and only the direction of a flow of a current is roughly illustrated. The two z-direction gradient-magnetic-field shield coils zGSC can be divided one by one on a x-y plane, and have a plane-symmetrical structure relative to such a plane.

Figure 5A:
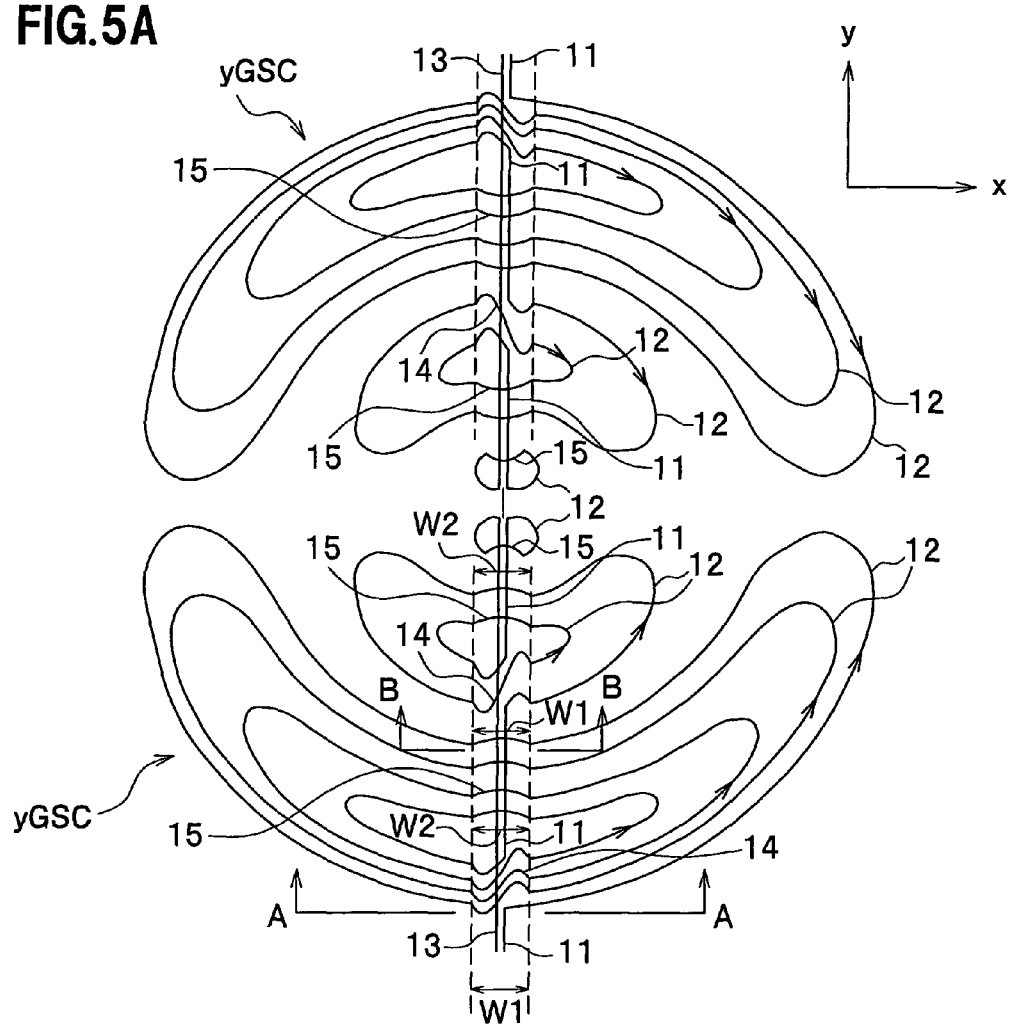
FIG. 5A is a pattern diagram of the y-direction gradient-magnetic-field shield coil of the gradient coil of the first embodiment.
Figure 5B:
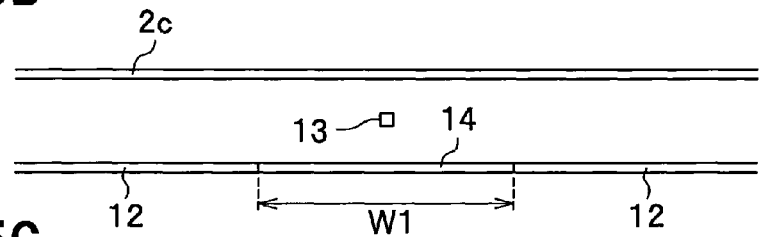
FIG. 5B is a cross-sectional view along a line A-A in FIG. 5A.
Figure 5C:
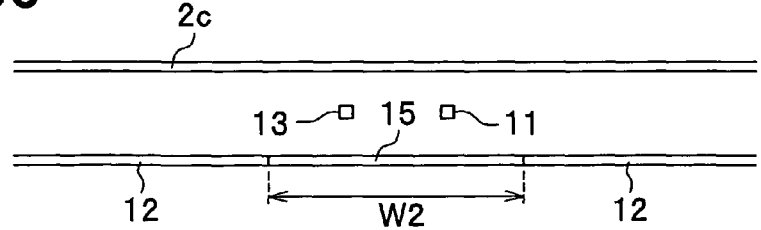
FIG. 5C is a cross-sectional view along a line B-B in FIG. 5A.

FIG. 5A is a pattern diagram of the y-direction gradient-magnetic-field shield coil yGSC, FIG. 5B is a cross-sectional view along a line A-A in FIG. 5A, and FIG. 5C is a cross-sectional view along a line B-B in FIG. 5A. The y-direction gradient-magnetic-field main coil yGMC has a coil pattern similar to that of the y-direction gradient-magnetic-field shield coil yGSC but slightly smaller than that. The x-direction gradient-magnetic-field shield coil xGSC has a coil pattern congruent with that of the y-direction gradient-magnetic-field shield coil yGSC rotated by 90 degrees. The y-direction gradient-magnetic-field main coil yGMC has a coil pattern congruent with that of the y-direction gradient-magnetic-field shield coil yGSC rotated by 90 degrees but slightly smaller than that.

As shown in FIG. 5A, the y-direction gradient-magnetic-field shield coil yGSC has a plurality of main lines 12 on a plane (coil surface). The plurality of main lines 12 are separately arranged (in the embodiment, three by three) in a plurality of areas. In a first area, the main lines 12 are arranged quadruply (multiply) in such a way that one main line 12 is arranged inwardly of an adjacent main line 12. In a second area, the main lines 12 are arranged doubly (multiply) in such a way that one main line 12 is arranged inwardly of an adjacent main line 12. In a third area, the main line 12 is arranged singly. A feeder line 11 for supplying power to the main lines 12 in individual areas and a return line 13 arranged along the feeder line 11 and allowing currents to return from the main lines 12 where power is supplied are also provided. A part where the feeder line 11 and the return line 13 step over the main line 12 is defined as a correction interval 15 in the main line 12, and in such a correction interval 15, the main line 12 is bypassed and folded convexly on the coil surface. Accordingly, even if an error magnetic field is generated by the feeder line 11 and the return line 13, such an error magnetic field can be canceled by a magnetic field generated by the main line 12 bypassed and folded convexly in the correction interval 15 in the vicinity of the feeder line 11 and the return line 13, so that it is possible to suppress any generation of an eddy current at the vacuumed container 2c or the like of the static-magnetic-filed coil device 2, resulting in improvement of the image quality of a cross-sectional image. Note that a width W2 of the correction interval 15 is set to be larger than a clearance between the feeder line 11 and the return line 13.

Each of the plurality of main lines 12 multiply (doubly and quadruply) arranged in the first area and the second area is formed in a looped shape having an opened part like U-shape. Such opened parts of the loops (U-shaped) are arranged in a line, and a connecting line 14 connects the adjacent main lines 12 together at this opened part. Such connection forms a spiral coil pattern in which multiple main lines 12 are connected together. Note that a width of such an opened part, i.e., a width (connecting width) W1 across the connecting line 14 to be discussed later is set to be wider than the line width of the return line 13. The connecting line 14 meanders in such a way that an angle relative to the return line 13 less than or equal to 90 degrees becomes smaller than an angle relative to the return line 13 less than or equal to 90 degrees when the adjacent main lines 12 are connected together with a straight line. The return line 13 is connected not only for connecting the foregoing areas, but also for drawing out a wiring outwardly of an outward main line 12 from the inward main lines 12 multiply arranged, and is so arranged as to overlap the connecting line 13. Accordingly, even if an error magnetic field is generated by the return line 13, such an error magnetic field can be canceled by a magnetic field generated by the connecting line 14 having large meandered inclination in the vicinity of the return line 13, so that it is possible to suppress any generation of an eddy current at the vacuumed container 2*c* or the like of the static-magnetic-field coil device 2, resulting in improvement of the image quality of a cross-sectional image.

As shown in FIG. 5B, the return line 13 is arranged between the connecting line 14 and the vacuumed container 2*c* of the static-magnetic-field coil device 2. That is, the return line 13 is arranged at a position closer to the vacuumed container 2*c* than a position of the connecting line 14. The intensity of an error magnetic field generated at the vacuumed container 2*c* is likely to be large because of the return line 13 located in the vicinity of the vacuumed container 2*c*, and in order to cancel such a large error magnetic field, the connecting line 14 meanders in such a way that an angle relative to the return line 13 less than or equal to 90 degrees becomes smaller than an angle relative to the return line 13 less than or equal to 90 degrees when the adjacent main lines 12 are connected together with a straight line so as to generate a large magnetic field at the vacuumed container 2*c* by the connecting line 14 spaced apart from the vacuumed container 2*c*.

As shown in FIG. 5C, the feeder line 11 and the return line 13 are arranged between the correction interval 15 of the main line 12 and the vacuumed container 2*c* of the static-magnetic-field coil device 2. That is, the feeder line 11 and the return line 13 are arranged at positions closer to the vacuumed container 2*c* than a position of the correction interval 15 of the main line 12. The intensity of error magnetic field generated at the vacuumed container 2*c* is likely to be large because of the feeder line 11 and the return line 13 both located in the vicinity of the vacuumed container 2*c*, and in order to cancel such a large error magnetic field, the level of folding the main line 12 convexly at the correction interval 15 is adjusted at the correction interval 15 spaced apart from the vacuumed container 2*c* so as to generate a large magnetic field at the vacuumed container 2*c* in accordance with the intensity of the error magnetic field.

Figure 6:
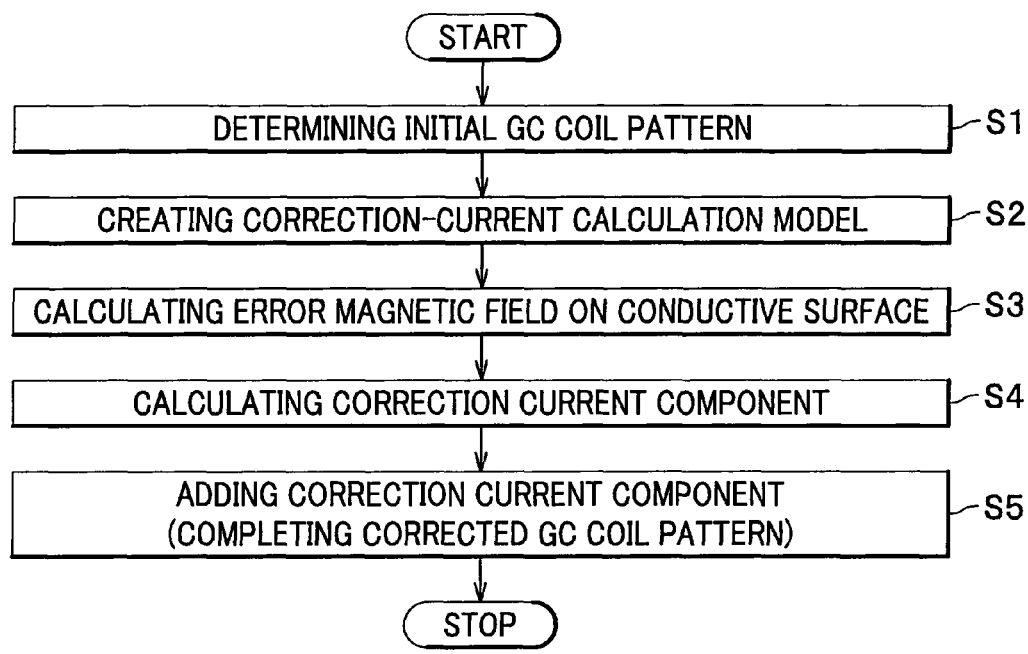
FIG. 6 is a flowchart showing a method of designing a coil pattern of the y-direction gradient-magnetic-field shield coil or the like in the gradient coil of the first embodiment.

FIG. 6 is a flowchart of a method of designing a coil pattern of the y-direction gradient-magnetic-field shield coil yGSC or the like of the gradient coil device 3 according to the first embodiment of the present invention.

Figure 7A:
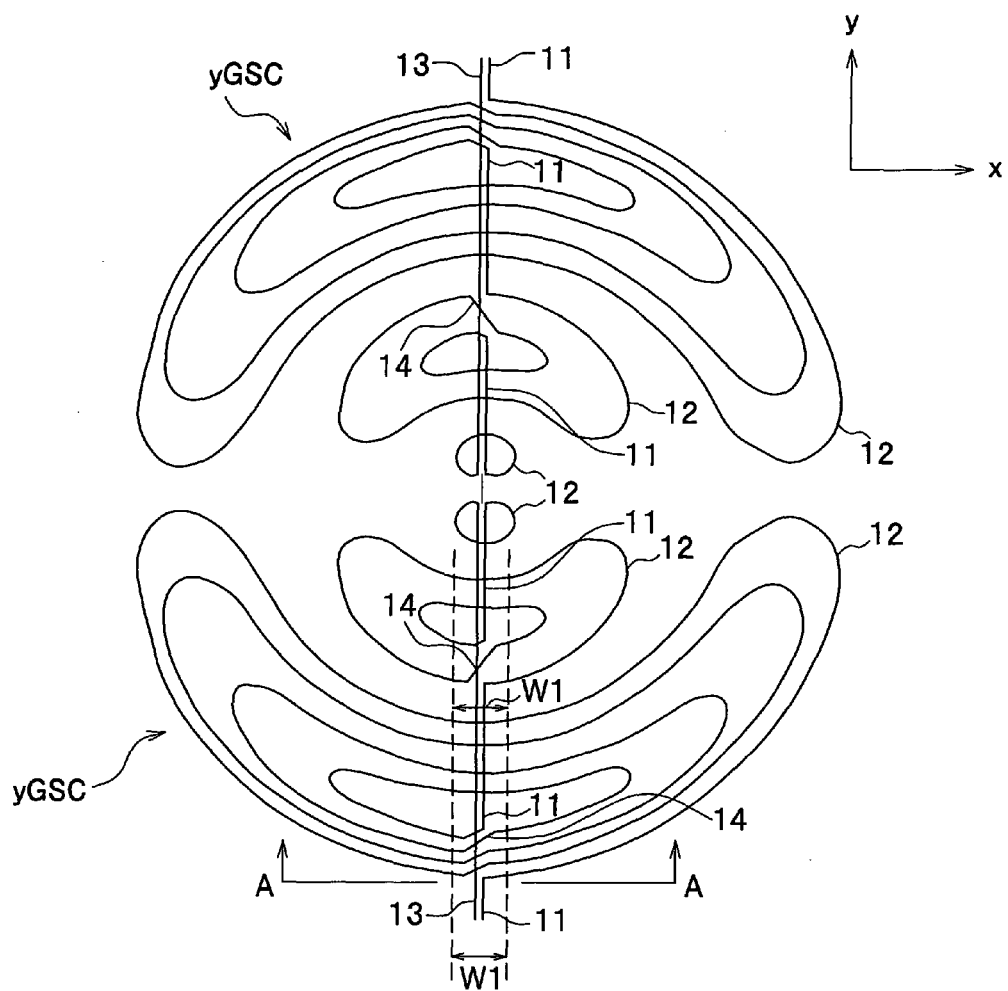
FIG. 7A is a diagram showing an example of an initial GC coil pattern prepared in step S1 of the coil pattern designing method.

First, a shape (including an arrangement position) of, in particular, the main line 12 of the y-direction gradient-magnetic-field shield coil yGSC or the like is calculated in step S1, and as shown in FIG. 7A, the connecting line 14 is set to be straight and is wired (connected) to the main line 12 to determine an initial GC coil pattern.

Figure 8:
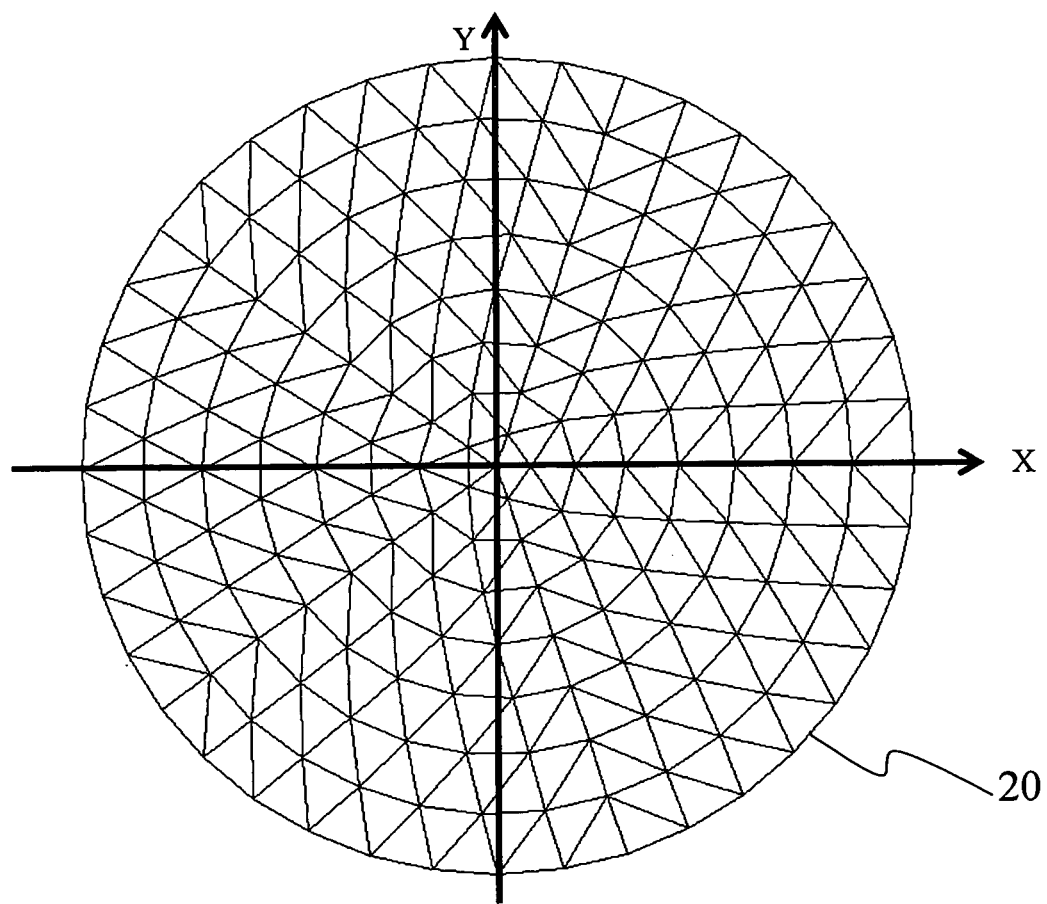
FIG. 8 is a diagram showing an example of a coil surface divided by finite elements (i.e., triangulated meshes) in step S2 of the coil pattern designing method.

In step S2, a coil surface 20 forming the initial GC coil pattern is divided by finite elements (i.e., triangulated meshes) as shown in FIG. 8, and a gradient-coil-correction-current calculation model is created with the finite elements. FIG. 8 is for a reference purpose only, and shows larger triangulated elements larger than ones used in an actual calculation.

Figure 7B:
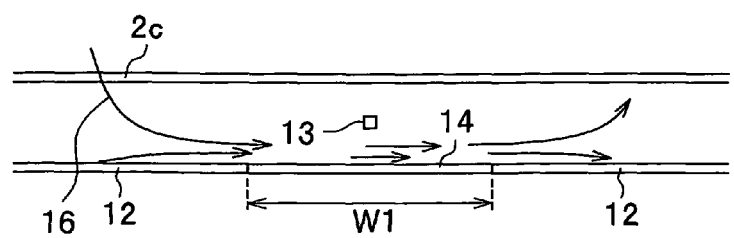
FIG. 7B is a cross-sectional view along a line A-A in FIG. 7A.
Figure 10:
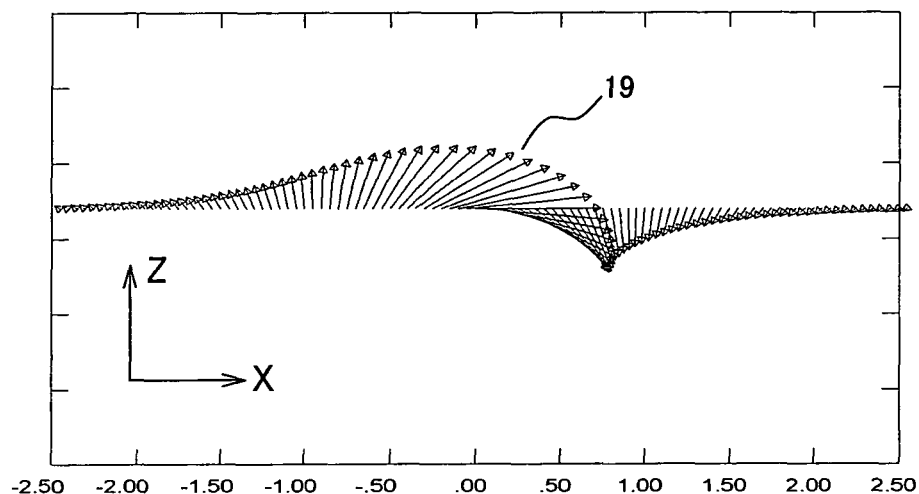
FIG. 10 is a distribution chart of error magnetic field components generated by a return line and a first connecting line over a vacuumed container (conductive object)

In step S3, an error magnetic field at the static-magnetic-field coil device 2 or the like is calculated based on the initial GC coil pattern prepared in the step S1. As shown in FIG. 7B, because the error magnetic field generates a magnetic line 16 passing through a conductive surface of the vacuumed container 2*c* or the like of the static-magnetic-field coil device 2, as shown in FIG. 10, the error magnetic field can be calculated by calculating distributions of direction/magnitude (intensity) 19 of a magnetic field entering into the conductive surface of the vacuumed container 2*c*.

Figure 9A:
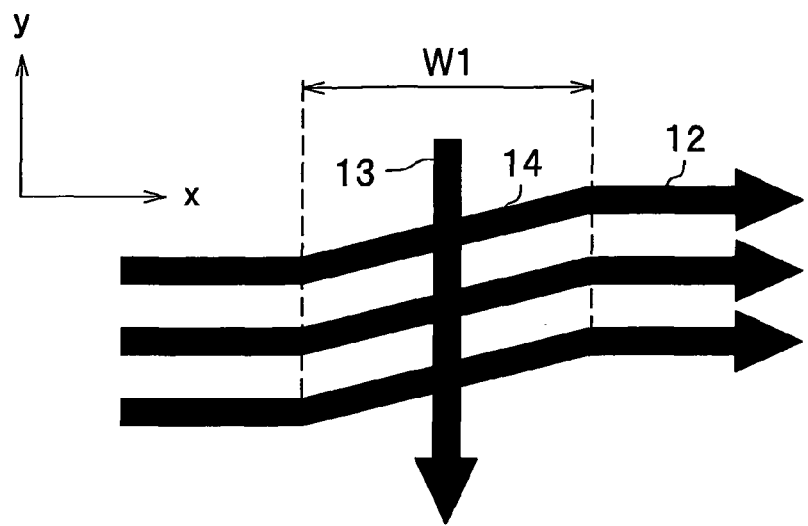
FIG. 9A is an enlarged view around a return line of the initial GC coil pattern prepared in the step S1 of the coil pattern designing method and a first connecting line thereof.
Figure 9B:
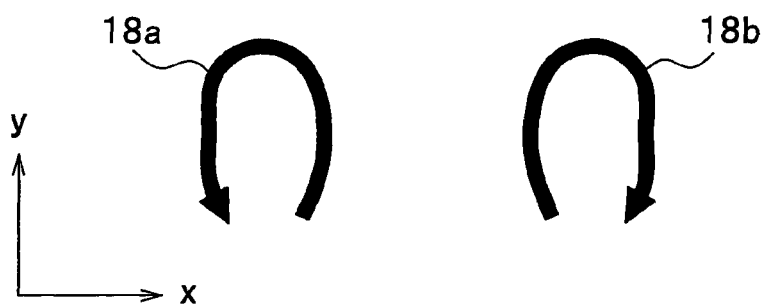
FIG. 9B is a conceptual diagram of a correction current (component) calculated in step S4.

In step S4, a correction current component for canceling the error magnetic field is calculated in such a manner as to exist over the coil surface. Accordingly, correction current components 18*a* and 18*b*, which are shown in FIG. 9B and exist over the coil surface where the connecting line 14 is located, can be calculated with respect to the return line 13 and connecting line 14 of the initial GC coil pattern shown in FIG. 9A.

More specifically, first, a current potential is given to a contact of the finite elements, and a current represented by a vector T indicating a current potential distribution with such a current potential as an element sets a current potential distribution T which cancels an error magnetic field B over a conductive surface. A current density vector can be expressed as a product of the gradient of a current potential by the normal vector of a current (coil) surface. By applying a technique of utilizing singular value decomposition to such an approximate solution method, it is possible to obtain a current potential T of a canceling current component which suppresses any generation of an eddy current and improves the precision of a magnetic field without any complexity.

When the current potential distribution T corresponding to the canceling current component are set by the foregoing fashion, a displacement of a conductor (coil) position is calculated next. From a distance d between conductors and a current Ic of the conductor, Ic/d is equivalent to the gradient of the current potential. Accordingly, the current potential T of the correction current component can be converted into a displacement of a conductor position by T/(gradient) where italic means the T is the local T at the position, not the vector describing the distribution. Moreover, when the initial GC coil pattern is set based on a current potential calculated value T0, a displacement of the conductor (coil) position can be calculated from a formula T/∇T0.

Note that a technique disclosed in the following literature can be applied for calculation of a correction current component: M. ABE, T. NAKAYAMA, S. OKAMURA, K. MATSUOKA, "A new technique to optimize coil winding path for the arbitrarily distributed magnetic field and application to a helical confinement system", Phys. Plasmas. Vol. 10, No. 4 (2003) 1022.

Figure 9C:
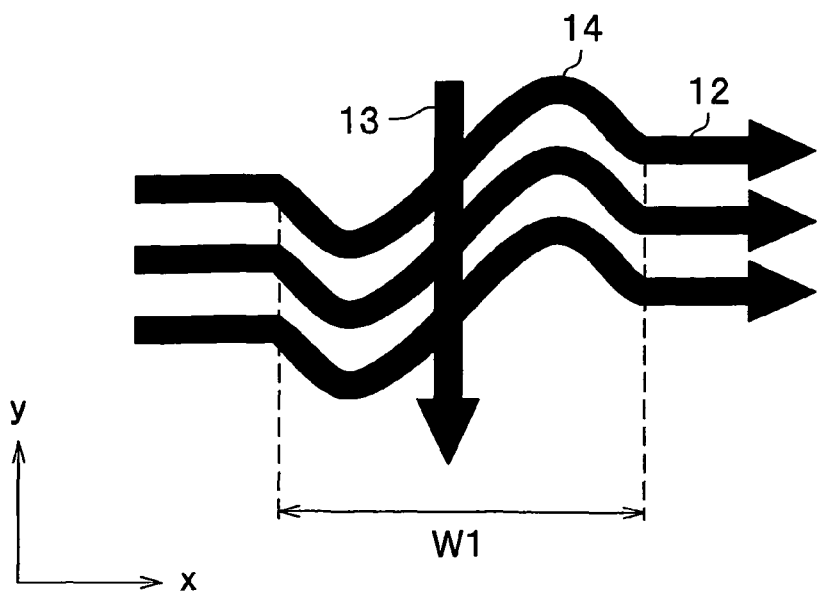
FIG. 9C is an enlarged view around a return line of a corrected GC coil pattern to which the correction current component is added in step S5 and a first connecting line thereof.

In step S5, the initial GC coil pattern is deformed based on the correction current component. The correction current component is added to a current component along the initial GC coil pattern, and a corrected GC coil pattern can be completed with the deformed current component as the coil pattern of the y-direction gradient-magnetic-field shield coil yGSC as shown in FIG. 5A. More specifically, the correction current components 18*a*, 18*b* shown in FIG. 9B are added and synthesized with respect to the current component along the connecting line 14 shown in FIG. 9A, and as shown in FIG. 9C, the connecting line 14 is changed so as to meander so that an angle relative to the return line 13 less than or equal to 90 degrees becomes smaller than an angle relative to the return line 13 less than or equal to 90 degrees when the adjacent main lines 12 are connected together by a straight line.

Figure 11:
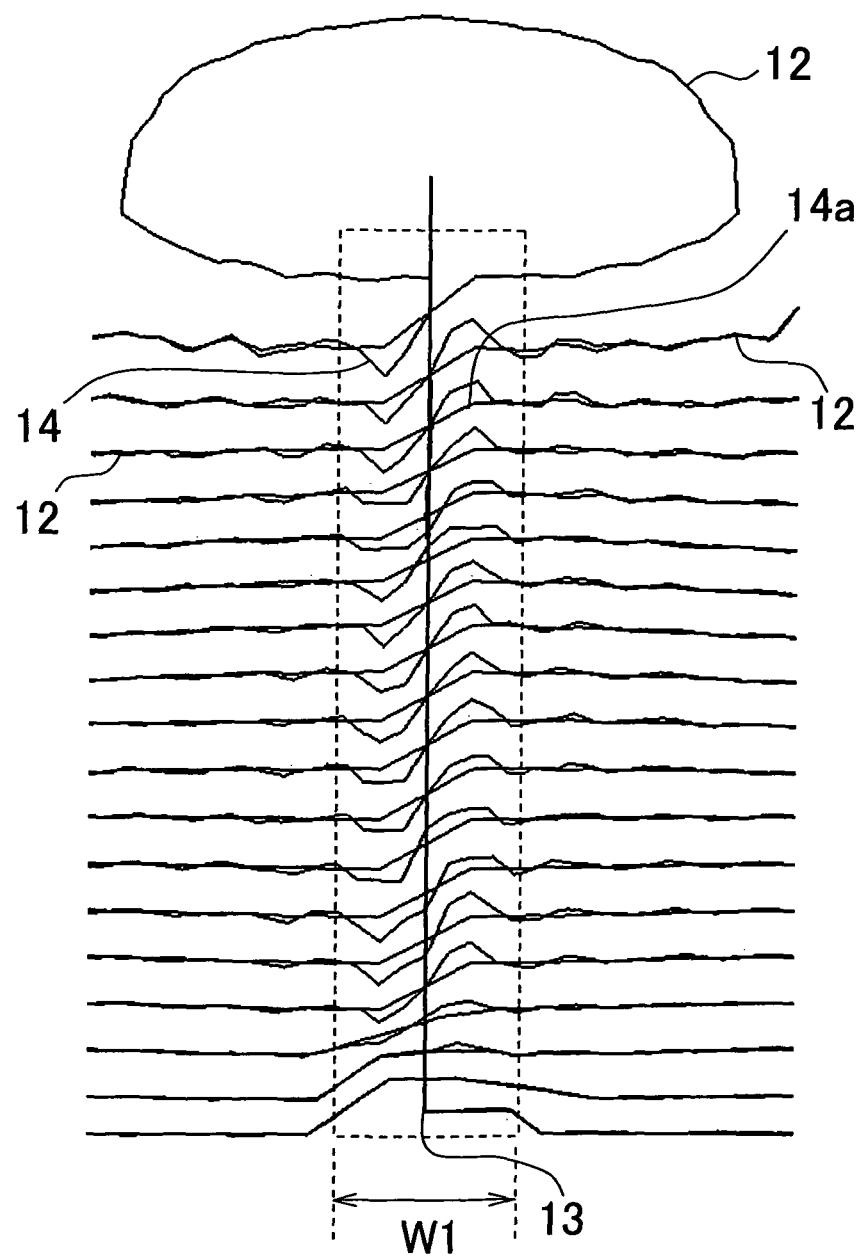
FIG. 11 is a diagram showing a change in flow of a current centroid of a GC coil pattern before and after a correction current component is added in the step S5.

FIG. 11 shows a connecting line 14*a* of the initial GC coil pattern and a connecting line 14 of the corrected GC coil pattern overlapped with each other. The connecting line 14 meanders in such a way that an angle relative to the return line 13 less than or equal to 90 degrees becomes smaller than an angle relative to the return line 13 less than or equal to 90 degrees when the adjacent main lines 12 are connected together by a straight line (14*a*) in an area where the connecting line 14 overlaps the return line 13. Note that flows of current centroid are shown as the connecting line 14 and the main line 12 of the initial GC coil pattern and of the corrected GC coil pattern. A current (coil) pattern is corrected (corrected in such a way that an area surrounded by the connecting line 14 and the connecting line 14a becomes small) in such a way that a magnetic moment below the return line 13 at the center of FIG. 11 becomes small, and is corrected in such a way that a magnetic moment thereabove becomes large after correction.

In the foregoing description, a method of obtaining a gradient of a current potential based on a conductor width and an original current potential calculation result, and a method of calculating a displacement of a conductor (coil) position corresponding to a correction current component are explained. The present invention is, however, not limited to such methods, and as explained with regard to FIG. 11, a method of performing correction in consideration of a magnetic moment can be employed. Because an area integration value of a current potential is a magnetic moment, such integration is performed for each area representing one turn of a coil surface or several turns thereof, and a magnitude of displacement of a conductor (coil) position is set in such a way that a product of an area surrounded by such a turn by a current becomes a magnitude of a magnetic moment to be changed. The same effect can be achieved by either method, and the correction GC coil pattern becomes a coil pattern which minimizes generation of an eddy current at a proximal conductive surface.

Next, with reference to FIG. 12, a modified example in which the main line 12 traverses a portion where reciprocating currents flow through the feeder line 11 and the return line 13 without the connecting line 14 will be explained. With reference to the flowchart of the coil pattern designing method, the method can be performed until the step S2 in the same fashion as the foregoing case.

Figure 12A:
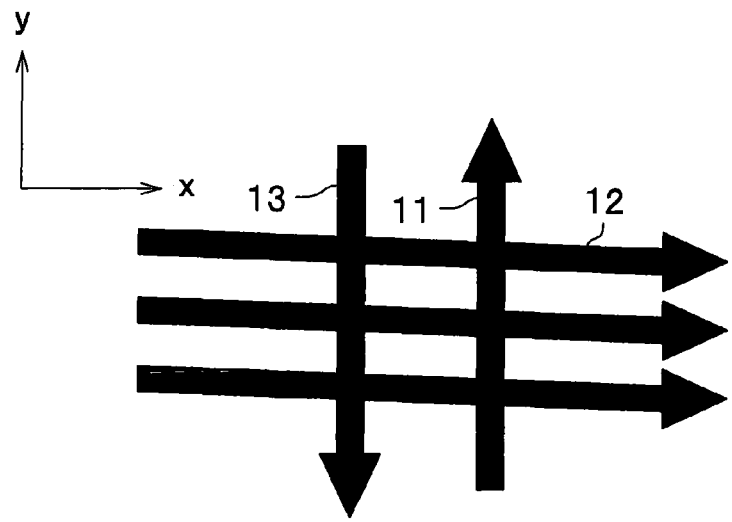
FIG. 12A is an enlarged view around a feeder line, a return line, and a main line of the initial GC coil pattern prepared in the step S1 of the coil pattern designing method.

In the step S3, an error magnetic field at the static-magnetic-field coil device 2 or the like is calculated based on the initial GC coil pattern prepared in the step S1. As shown in FIG. 12A, in the initial GC coil pattern, the main line 12 traverses a portion where reciprocating currents flow through the feeder line 11 and the return line 13.

In the step S4, a correction current component which cancels the error magnetic field is calculated in such a manner as to be exist over a coil surface. Accordingly, a correction current component 21 shown in FIG. 12B which exists over the coil surface where the main line 12 is located can be calculated with respect to the feeder line 11, the return line 13, and the main line 12 of the initial GC coil pattern shown in FIG. 12A.

Figure 12B:
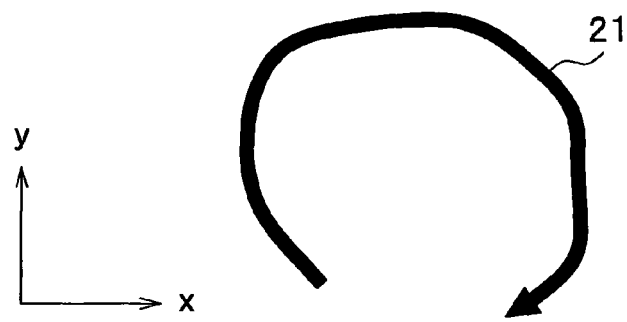
FIG. 12B is a conceptual diagram showing a correction current (component) calculated in the step S4.
Figure 12C:
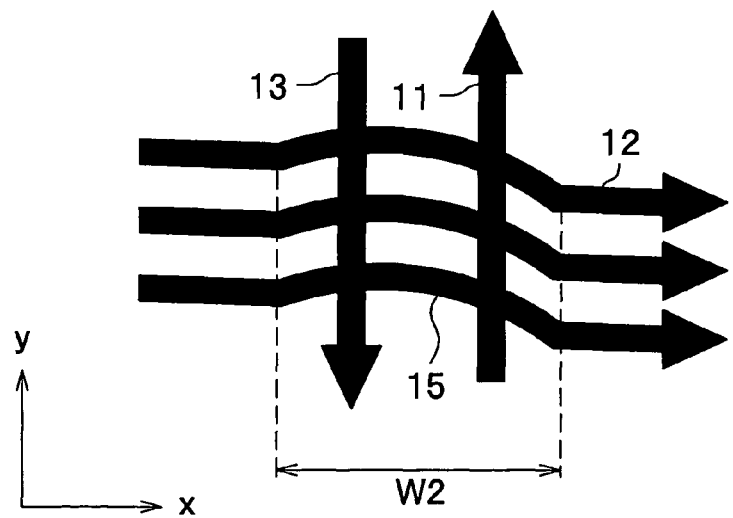
FIG. 12C is an enlarged view around a feeder line, a return line, and a second connecting line of a corrected GC coil pattern to which a correction current component is added in the step S5.

In the step S5, the correction current component 21 shown in FIG. 12B is added and synthesized with respect to the main line 12 shown in FIG. 12A, and as shown in FIG. 12C, the main line 12 bypasses the feeder line 11 and the return line 13 by being curved convexly at a correction interval 15. Such a corrected GC coil pattern can also reduce the error magnetic field which generates an eddy current.

As explained above, according to the first embodiment, in designing of a gradient coil, an error magnetic field passing through a proximal conductive surface like the vacuumed container 2c can be reduced, and any generation of an eddy current is thus suppressed, so that it is possible to provide a clear diagnostic image. Also, by suppressing any generation of an eddy current, it is possible to suppress any vibration which originates from the eddy current.

Second Embodiment

Figure 13A:
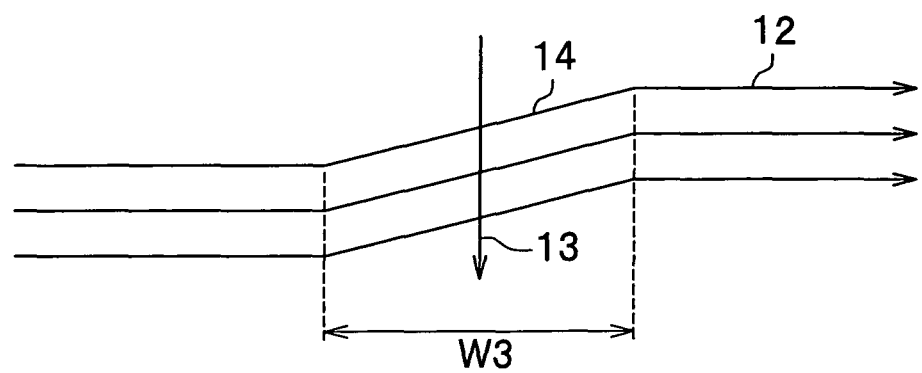
FIG. 13A is a pattern diagram around a return line of a y-direction gradient-magnetic-field shield coil of a gradient coil according to a second embodiment of the present invention, and around a first connecting line thereof.
Figure 13B:
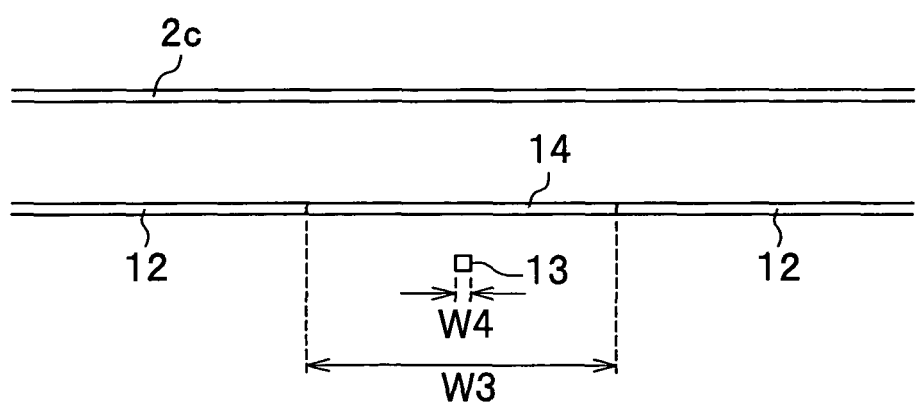
FIG. 13B is a cross-sectional view around the return line and the first connecting line.

FIG. 13A is a pattern diagram around a return line 13 and a connecting line 14 of a y-direction gradient-magnetic-field shield coil of a gradient coil according to the second embodiment of the present invention. FIG. 13B is a cross-sectional view around the return line 13 and the connecting line 14. The second embodiment differs from the first embodiment in that as shown in FIG. 13B, the return line 13 is arranged opposite to the vacuumed container 2c across the connecting line 14. Accordingly, the return line 13 is arranged at a position farther than a position of the connecting line 14 from the vacuumed container 2c. The intensity of an error magnetic field generated at the vacuumed container 2c by the return line 13 apart from the vacuumed container 2c is small, and in order to cancel such a small error magnetic field, it is appropriate to generate a small magnetic field by the connecting line 14 near the vacuumed container 2c. Therefore, the connecting line 14 need not to meander in such a way that an angle relative to the return line 13 less than or equal to 90 degrees becomes smaller than an angle relative to the return line 13 less than or equal to 90 when the adjacent main lines 12 are connected together with a straight line. Also, in the second embodiment, in order to cancel such a small error magnetic field, the adjacent main lines 12 are connected together with the straight connecting line 14, and the connecting width W3 is set to be variable to adjust the inclination of connecting line 14.

FIGS. 14A to 14D show a result when the coil pattern designing method explained in the first embodiment is applied to the second embodiment. FIGS. 14A to 14D are distribution charts of a direction and magnitude of an error magnetic field over the vacuumed container (conductive object) generated by the return line 13 and the connecting line 14. FIG. 14A shows a case in which the ratio of the connecting width W3 relative to the width W4 of the return line 13 is four times. FIG. 14B shows case in which the ratio of the connecting width W3 relative to the width W4 is six times. FIG. 14C shows a case in which the ratio of the connecting width W3 relative to the width W4 is eight times. FIG. 14D shows a case in which the ratio of the connecting width W3 relative to the width W4 is ten times. The smaller the magnitude of the error magnetic field in the z-direction across the vacuumed container (conductive object) 2c, the less a generated eddy current. When the ratio is eight times or so, the magnitude of the error magnetic field in the z-direction becomes smallest. The larger the ratio, the larger the magnitude of the error magnetic field in the z-direction. Also, the smaller the ratio, the larger the magnitude of the error magnetic field in the z-direction. Accordingly, it becomes clear that if the ratio is greater than or equal to four times and is less than or equal to ten times, the magnitude of the error magnetic field in the z-direction can be suppressed. When such a ratio is adopted, it is possible to suppress any generation of an eddy current, resulting in improvement of the image quality of a cross-sectional image.

What is claimed is:
1. A gradient coil device comprising:
   a first coil which generates a linear magnetic field distribution at an imaging region of a magnetic resonance imaging device; and
   a second coil which suppresses any leakage of a magnetic field from the first coil to a static-magnetic-field coil that generates a uniform magnetic field distribution at the imaging region,
   wherein a connecting line of at least either one of the first coil and the second coil intersecting with a return line from a spiral coil pattern meanders so that the connecting line goes down, goes up and goes down in a trough-like and crest-like manner, as a connecting line coil pattern.

2. A gradient coil device according to claim 1, wherein
   wherein at least either one of the first coil and the second coil includes a coil pattern having an bypassed interval which intersects with a feeder line to a spiral coil pattern and a return line from the coil pattern.
3. A magnetic resonance imaging device comprising:
   the gradient coil device according to claim 2; and
   a static-magnetic-field coil device which is arranged adjacent to the gradient coil device, and which generates a uniform static magnetic field at an imaging region of the magnetic resonance imaging device.
4. A magnetic resonance imaging device comprising:
   the gradient coil device according to claim 1; and
   a static-magnetic-field coil device which is arranged adjacent to the gradient coil device, and which generates a uniform static magnetic field at an imaging region of the magnetic resonance imaging device.
5. The gradient coil device as claimed in claim 1, wherein the connecting line more specifically meanders in a sinusoidal-like pattern.
6. A gradient coil device comprising:
   a first coil which generates a linear magnetic field distribution at an imaging region of a magnetic resonance imaging device; and
   a second coil which suppresses any leakage of a magnetic field from the first coil to a static-magnetic-field coil that generates a uniform magnetic field distribution at the imaging region,
   wherein a connecting line of at least either one of the first coil and the second coil intersecting with a return line from a spiral coil pattern meanders initially in a same direction as a direction as the return line, then reverses in an opposite direction to the same direction, and then reverses in the same direction in a trough-like and crest-like manner, as a connecting line coil pattern.
7. A gradient coil device according to claim 6, wherein
   wherein at least either one of the first coil and the second coil includes a coil pattern having an bypassed interval which intersects with a feeder line to a spiral coil pattern and a return line from the coil pattern.
8. A magnetic resonance imaging (MRI) apparatus comprising:
   a gradient coil device comprising:
      a first coil which generates a linear magnetic field distribution at an imaging region of a magnetic resonance imaging device; and
      a second coil which suppresses any leakage of a magnetic field from the first coil to a static-magnetic-field coil that generates a uniform magnetic field distribution at the imaging region,
      wherein a connecting line of at least either one of the first coil and the second coil intersecting with a return line from a spiral coil pattern meanders so that the connecting line goes down, goes up and goes down in a trough-like and crest-like manner, as a connecting line coil pattern.
9. An MRI apparatus according to claim 8, wherein
   wherein at least either one of the first coil and the second coil includes a coil pattern having an bypassed interval which intersects with a feeder line to a spiral coil pattern and a return line from the coil pattern.
10. An MRI apparatus as claimed in claim 8, wherein the connecting line more specifically meanders in a sinusoidal-like pattern.

* * * * *